United States Patent [19]

Leonard

[11] 4,184,257
[45] Jan. 22, 1980

[54] DENTAL HANDPIECE

[75] Inventor: Henri Leonard, Besancon, France

[73] Assignee: Micro-Mega S.A., France

[21] Appl. No.: 867,101

[22] Filed: Jan. 5, 1978

[30] Foreign Application Priority Data

Jan. 26, 1977 [FR] France .................... 77 02685

[51] Int. Cl.² ............................................ A61C 13/22
[52] U.S. Cl. ...................................................... 433/82
[58] Field of Search ................................. 32/27, 28, 22

[56] References Cited

U.S. PATENT DOCUMENTS

| | | | |
|---|---|---|---|
| 3,169,504 | 2/1965 | Gruber | 277/166 UX |
| 3,218,028 | 11/1965 | Borden | 32/27 |
| 4,007,529 | 2/1977 | Fleer | 32/27 |
| 4,080,737 | 3/1978 | Fleer | 32/22 |

Primary Examiner—Robert Peshock
Attorney, Agent, or Firm—Robert E. Burns; Emmanuel J. Lobato; Bruce L. Adams

[57] ABSTRACT

A dental handpiece comprises two sections, notably in the case of a contra-angle, which are rigidly assembled and both provided with an aligned passage for delivering the liquid to be atomized to the head of the handpiece, said passage being incorporated in the wall of each section and the joint between the two sections comprises an annular seal fitted in a recess surrounding the passage and formed in one section, the length of this seal being slightly greater than the depth of the recess, so that the outer edge of the seal tightly engages the registering face formed in the other section, this arrangement being adaptable to all dental handpieces provided with internal passage means for the liquid intended for cooling the tool.

8 Claims, 4 Drawing Figures

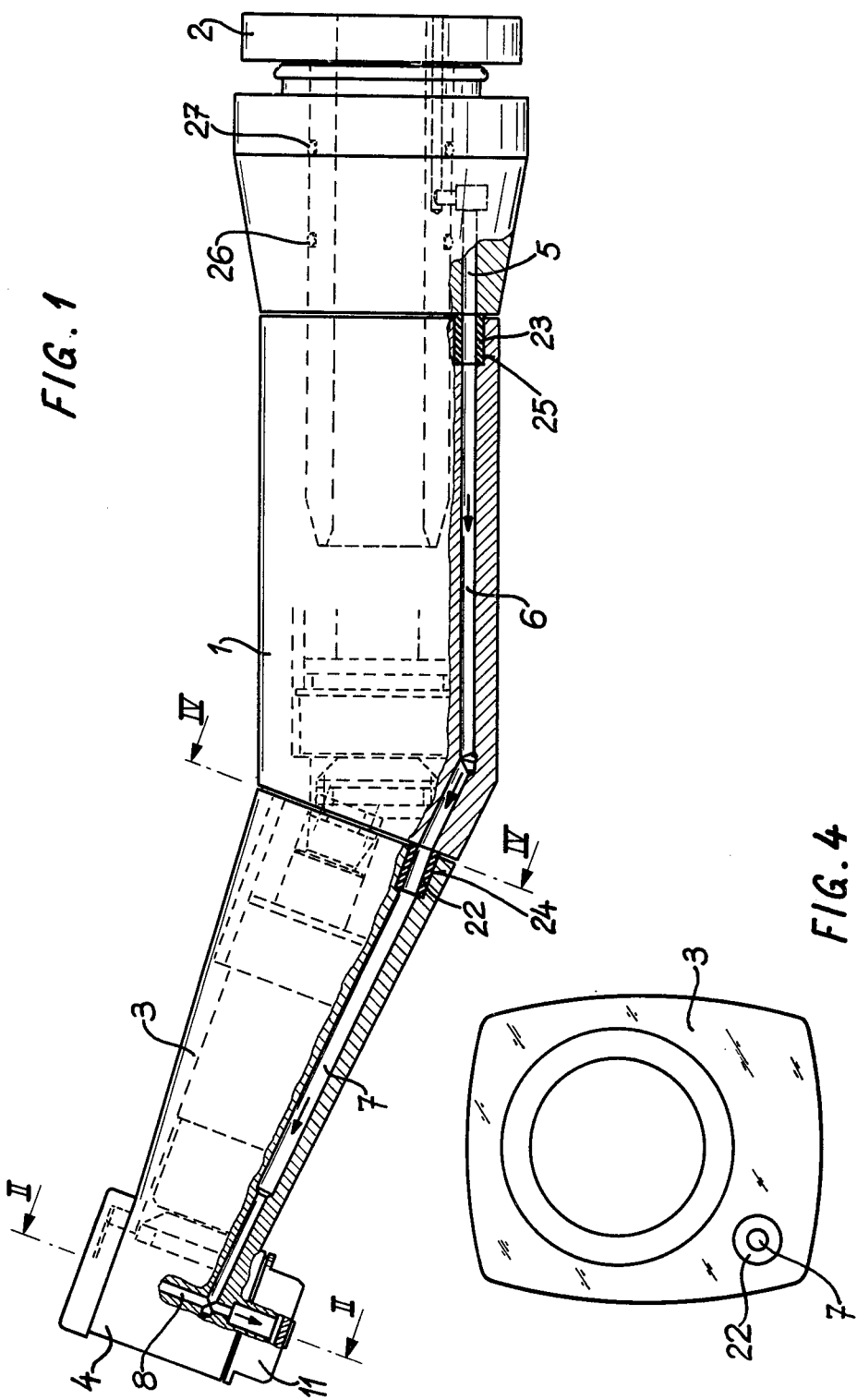

DENTAL HANDPIECE

BACKGROUND OF THE INVENTION

The present invention relates to a dental hand tool holder or handpiece consisting of at least two interconnected sections and incorporating a passage or conduit for delivering a liquid to be atomized to the head of the handpiece.

DESCRIPTION OF THE PRIOR ART

Dental handpieces are already known which comprise an external conduit for supplying liquid to be atomized to the head of a contra-angle, this conduit consisting of a flexible plastic hose detachably connected to a metal inlet pipe welded in turn to the head of the bent handpiece, this arrangement permitting the use of the liquid to be atomized for cooling the head of the contra-angle. However, this structure has several shortcomings. On the one hand, the external plastic hose passes over or under the dentist's fingers which, at the same time, grip the tool holder, and this may prove detrimental. On the other hand, when the contra-angle is coupled or uncoupled with respect to the motor, this plastic hose must be connected or disconnected from the metal pipe, this involving an additional time-robbing operation.

Besides, it is also known to provide an internal passage or conduit extending longitudinally through the contra-angle for directing the liquid to be atomized to the head, this passage opening directly at the lower portion of the head into an annular chamber having a plurality of ejection orifices formed therein. In this case, the passage must also be connected via an external hose or pipe to the source of liquid.

Up to now, no reliable arrangement comprising a completely internal supply passage or conduit has been proposed for a dental handpiece consisting of at least two sections, due to the difficulty of obtaining a satisfactory fluid-tightness at the joint or coupling between the two sections.

DESCRIPTION OF THE INVENTION

It is the essential object of this invention to avoid the inconveniences of prior art structures by providing a dental handpiece characterized in that the passage for delivering fluid under pressure to be atomized at the head of a handpiece consisting of two sections forming a contra angle with each other is incorporated in the wall of each section and that an annular seal is provided at the joint between said two section, said seal being housed in a recess formed around the inner passage on the end face of one of the two sections, the height or longitudinal dimension of the seal being slightly greater than the depth of the recess, whereby said seal projects somewhat from said face and is caused to engage in a fluid-tight manner the registering end face of the other section of the handpiece.

Moreover, in the case of a dental handpiece comprising a separate head the problem of cooling the head arises; up to now, this problem was solved by using a metal tube welded to the head of the contra-angle, the liquid being caused to flow through said tube, as described hereinabove.

This problem is also solved by the present invention according to a complementary feature by providing in a dental handpiece equipped with a handpiece head having its axis perpendicular to the axis of the adjacent section of the tool holder, notably a contra-angle, an internal passage or conduit adapted to deliver a cooling liquid to be atomized to the head into a circular chamber; said chamber surrounds the tool or instrument in the lower portion of said head, and comprises a plurality of small orifices through which the liquid can escape to form as many jets directed towards the tool portion projecting from said head; said dental handpiece being further characterized in that the internal passage opens into at least one channel formed in the peripheral wall of said head through at least one fraction of the height thereof to permit the efficient cooling of the head, one end of said channel communicating directly with said circular chamber.

Thus, the sprinkling spray has the twofold function of cooling the milled tooth portion and cooling the head of the handpiece.

According to another preferred form of embodiment of this invention, the channel end opposite the one communicating directly with said circular chamber opens into an annular groove formed in the upper portion of the head to permit the liquid circulation.

With this arrangement, the cooling of the head of the hand tool holder is improved considerably.

BRIEF DESCRIPTION OF THE DRAWING

FIG. 1 is a side elevational view, with parts broken away, of a dental handpiece according to this invention;

FIG. 4 is an end view of the rear face of the front section of the handpiece, as seen in the direction of the arrows IV—IV of FIG. 1.

DESCRIPTION OF THE PREFERRED EMBODIMENT

Figure 3:
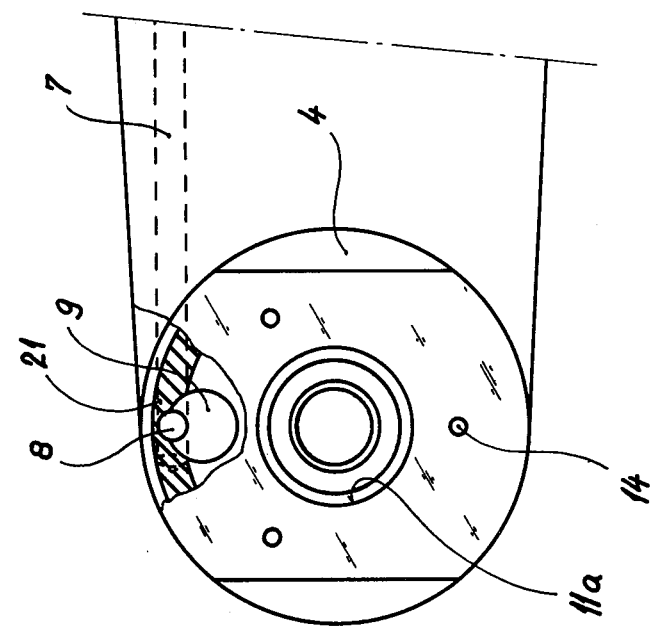
FIG. 3 is a view from beneath of the head of FIG. 2, with a part broken away.
Figure 2:
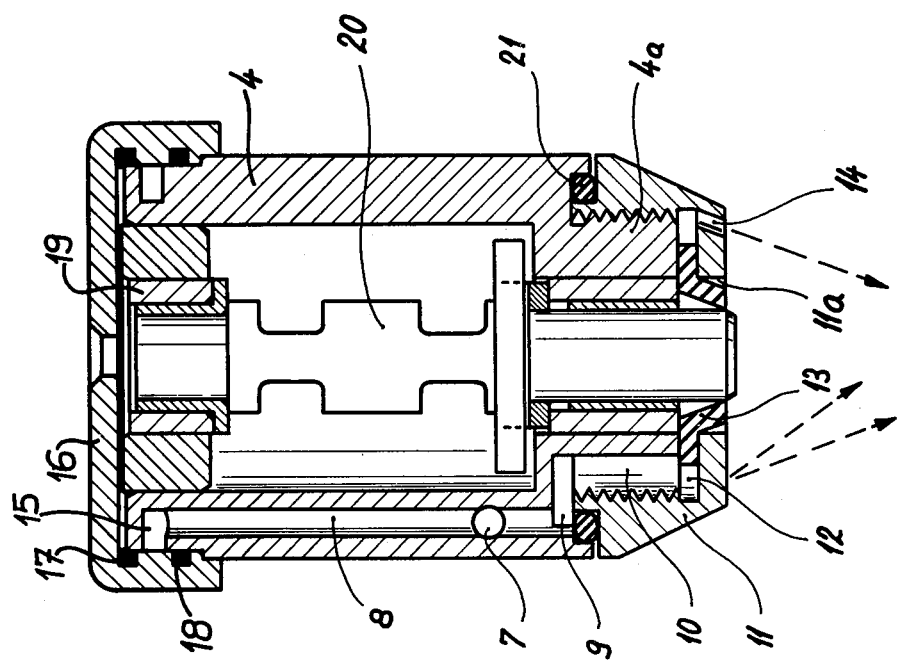
FIG. 2 is a section taken along the axis II—II of the head, showing the head alone.

The dental handpiece, in the present case of the contra-angle type, comprises two sections, i.e. a rear section 1 fitting on the motor 2 and a front section 3 provided with a head 4 for securing the tool (not shown), said front section 3 being adapted to be coupled to the rear section 1 and extending obliquely therefrom. The cross sectional contour of the handpiece body (FIG. 4) is not round; it is preferably rectangular with convex sides. An internal passage or conduit 5,6,7 for feeding cooling fluid to the head is formed through the motor 2, rear section 1 and front section 3 of the assembly; as shown in FIG. 4, this passage is drilled longitudinally through one corner of the handpiece body.

The necessary fluid-tightness between the internal passages of the various sections of the handpiece is obtained by means of tubular seals 22,23 fitted in recesses 24,25, respectively and formed concentrically to the passage in the end face of one of the two members to be assembled, the length of each seal being slightly greater than the depth of the corresponding recess so that a short longitudinal portion of the seal projects from the end face of the relevant member when the hand tool handpiece is disassembled and is compressed against said face in the assembled condition of the handpiece.

In the motor body 2 the fluid-tightness between the motor and the contra-angle is also provided by means of a pair of annular seals 26 and 27.

The passage 7 drilled through the front section 3 opens into a hole 8 drilled through the outer peripheral wall of head 4. This hole 8 extends substantially at right angles to the direction of passage 7 and the latter is substantially parallel to the nearest outer generatrix of front section 3. A circular cavity 9 is milled to cause the hole 8 to communicate with another hole 10 drilled in a nose cap 11. The latter is provided with a central aperture 11a and screwed on the reduced screw-threaded end 4a of head 4 in order to provide in conjunction with this reduced end 4a of head 4 an annular chamber 12 closed by a flanged frusto-conical and annular gasket 13 concentric to said central aperture 11a. This gasket 13 is compressed between the inner wall of nose cap 11 and the reduced end portion 4a of head 4, and projects somewhat into said central aperture 11a. The necessary fluid-tightness is also obtained by means of an O-ring 21 compressed between the base of nose cap 11 and the adjacent, non-reduced end of head 4. The circular chamber 12 has formed therein three oblique small orifices 14 through which the cooling liquid escapes in the form of jets directed towards the milling cutter (not shown).

In the form of embodiment illustrated, the opposite end of hole 8 opens into an annular groove 15 formed in the wall of the upper end portion of head 4 and closed by a back cap 16 force fitted on rear end of head 4. A pair of O-rings 17,18 are fitted in inner grooves of the back cap 16 for sealing the chamber formed by this groove. The purpose of this annular groove 15 is to permit the circulation of cooling fluid and thus improve the cooling of the bearing 19 in which the shaft 20 adapted to clamp the milling cutter is rotatably mounted.

In a modified embodiment the hole 8 may be a blind hole closed at its upper or back end and having a length corresponding substantially to the head length. Besides, a plurality of holes 8 may be disposed at spaced angular intervals around the head periphery, these holes 8 opening or not into an upper or intermediate annular chamber and being interconnected by a lower peripheral groove.

Though the present invention has been described hereinabove with reference to its application to a handpiece of the contra-angle type, it will readily occur to those conversant with the art that the invention is also applicable to any handpiece provided with means for cooling the tool, notably to hand tool holders comprising a head or mandrel for clamping the tool, such as an angled or orthogonal tool holder.

What is claimed is:

1. Dental handpiece comprising at least two interconnected sections, namely a rear section and a front section forming a contra-angle with said rear section, said front section having at its forward end an integral tool-holding head portion disposed at right angles to the longitudinal axis of said front section and including a tool-clamping shaft, said head portion having an annular internal chamber formed around said tool-clamping shaft and an internal longitudinal passage extending from said annular chamber longitudinally of the axis of said tool-clamping shaft, said sections having formed in the walls thereof an internal fluid supply passageway extending from said longitudinal passage to the rear end of said rear section to supply fluid to said annular chamber, said passageway being eccentric of the longitudinal axis of said sections and a portion of said passageway in one of said sections adjacent the junction between said section being enlarged to form a recess, a tubular seal received in said recess and having a length slightly greater than the depth of said recess whereby said seal projects slightly from the end face of the respective section and tightly engages the abutting end face of the adjacent section to provide a fluid-tight seal and said head portion having small orifices opening from said annular chamber to the front face of said head portion around said tool-clamping shaft for directing liquid jets toward a tool carried externally of said head portion by said clamping shaft.

2. Dental handpiece according to claim 1, wherein said longitudinal passage extends substantially the length of said head portion to cool said head portion.

3. Dental handpiece according to claim 2, wherein a bearing for said tool-clamping shaft is provided in said head portion, and wherein an annular groove in said head portion communicates with said longitudinal passage and surrounds said bearing to cool said bearing.

4. Dental handpiece according to claim 3, wherein said annular groove is defined by a groove around an upper end portion of said head portion and a cap fitting on said grooved end portion with O-rings at opposite sides of said annular groove to provide a seal.

5. Dental handpiece according to claim 1, further comprising a motor section joined to the rear end of said rear section and having an internal passageway forming a continuation of said supply passageway in said front and rear sections, said passageway having in one of said rear and motor sections having an enlarged portion adjacent the junction between said rear and motor sections to form a second recess, a second tubular seal received in said second recess and having a length slightly greater than the depth of said second recess, whereby said second seal projects slightly from the end face of the respective section and tightly engages the abutting end face of the adjacent section to form a fluid-tight seal.

6. Dental handpiece according to claim 1, wherein a plurality of parallel passages disposed at spaced angular intervals near the outer periphery of said head are interconnected by an annular groove.

7. Dental handpiece according to claim 1, wherein said annular chamber is bounded by the outer face of a reduced front end of said head portion, the inner wall of a nose cap formed with a central aperture and screwed on said head portion, and an annular, flanged, frusto-conical and annular gasket surrounding said central aperture and compressed between said reduced head front end and said nose cap.

8. Dental handpiece according to claim 1, wherein the cross-sectional contour of said sections is generally rectangular with convex sides, and said supply passageway is formed close to and parallel to one corner of said rectangle.

* * * * *